United States Patent [19]
Weinstein et al.

[11] 4,245,042
[45] Jan. 13, 1981

[54] DEVICE FOR HARVESTING CELL CULTURES

[75] Inventors: Yacob Weinstein, Rehovot; Jehoshua Wolowelsky, Ramat Gan; Nurit Gideoni, Rehovot, all of Israel

[73] Assignee: Yeda Research and Development Co. Ltd., Rehovot, Israel

[21] Appl. No.: 5,587

[22] Filed: Jan. 22, 1979

[30] Foreign Application Priority Data

Jan. 26, 1978 [IL] Israel ............... 53893

[51] Int. Cl.³ ............................... C12Q 1/24
[52] U.S. Cl. ............................ 435/30; 435/261; 435/311; 422/101
[58] Field of Search ............... 435/311, 284, 317, 30, 435/261, 292; 422/101

[56] References Cited

U.S. PATENT DOCUMENTS

| | | | |
|---|---|---|---|
| 3,319,792 | 5/1967 | Leder et al. | 422/101 X |
| 3,838,978 | 10/1974 | Eddleman | 422/101 |
| 3,888,770 | 6/1975 | Avital et al. | 422/101 X |
| 4,167,875 | 9/1979 | Meakin | 422/101 X |

Primary Examiner—R. B. Penland
Attorney, Agent, or Firm—Browdy and Neimark

[57] ABSTRACT

The present invention relates to a device for harvesting cells from a plurality of wells of a standard cell culture plate. Two complementary blocks, a lower and an upper one, are adapted to be attached with each other by suitable mechanical means to form a tight fit, the lower block being provided with a channel-formed conduit attached with an external source of a washing fluid, the flow of which is controlled by valve means. The conduit is connected with a plurality of downwardly pointing tubelets which are spaced in such manner that each one of them fits into a well of the culture plate, thus providing for the possibility of introducing at will washing fluid into the wells in the culture plate. Further tubes are provided which point in the same direction, each of which is connected with an outlet at the upper face of the lower block; an O-ring is provided substantially flush with the upper face of the block at each of the outlets. A central conduit is provided in the upper block, adapted to be connected with a vacuum source. The central conduit is connected via conduits connected therewith to each of the outlets at the upper face of the lower block, forming a tight connection via the O-rings. Cell cultures from a plurality of cells may be simultaneously harvested by means of this device.

6 Claims, 1 Drawing Figure

DEVICE FOR HARVESTING CELL CULTURES

BACKGROUND OF THE INVENTION

Culturing of cells for various diagnostic and research purposes is a standard technique. The cultivation of cell populations, such as lymphocytes, is used in tests of tissue compatibility, in the evaluation of the response of cells to certain types of drugs, antigens, allergens, etc. Cellular response is measured by the incorporation of radioactive tagging agents into the cell constituents. Cells are nowadays cultivated in standarized culture plates, generally having a plurality of 12 individual wells, of certain size and spacing. Such cell cultures are harvested by various devices, some of these quite sophisticated, but also rather complicated and expensive.

SUMMARY

The present invention relates to a cell harvester for the rapid and convenient harvesting of a predetermined number of cell cultures, for their application to a filter medium, and preparation for their subsequent transfer to evaluation means. According to a preferred embodiment there is provided a device for the simultaneous harvesting of 24 cell cultures, for the transfer of the cells to a filter medium, such as filter paper, for the washing of the cell culture wells and for the washing of the cell cultures on the filter medium, and for the subsequent evaluation of the collected cultures, generally by determination of radioactivity of the radioactive tag.

The novel cell harvesting device comprises two blocks with throughgoing channels and conduits, means for connecting to a vacuum source and to a source of washing fluid, and individual aspiration and flushing means being provided for the simultaneous harvesting and washing of the wells in a standard cell culture plate. The entire device is connected by means of a single conduit to the vacuum source, and by a single conduit to the source of washing solution, thus providing a simple, convenient and inexpensive apparatus. The novel device is described in greater detail in the following description.

BRIEF DESCRIPTION OF A PREFERRED EMBODIMENT

Figure 1:
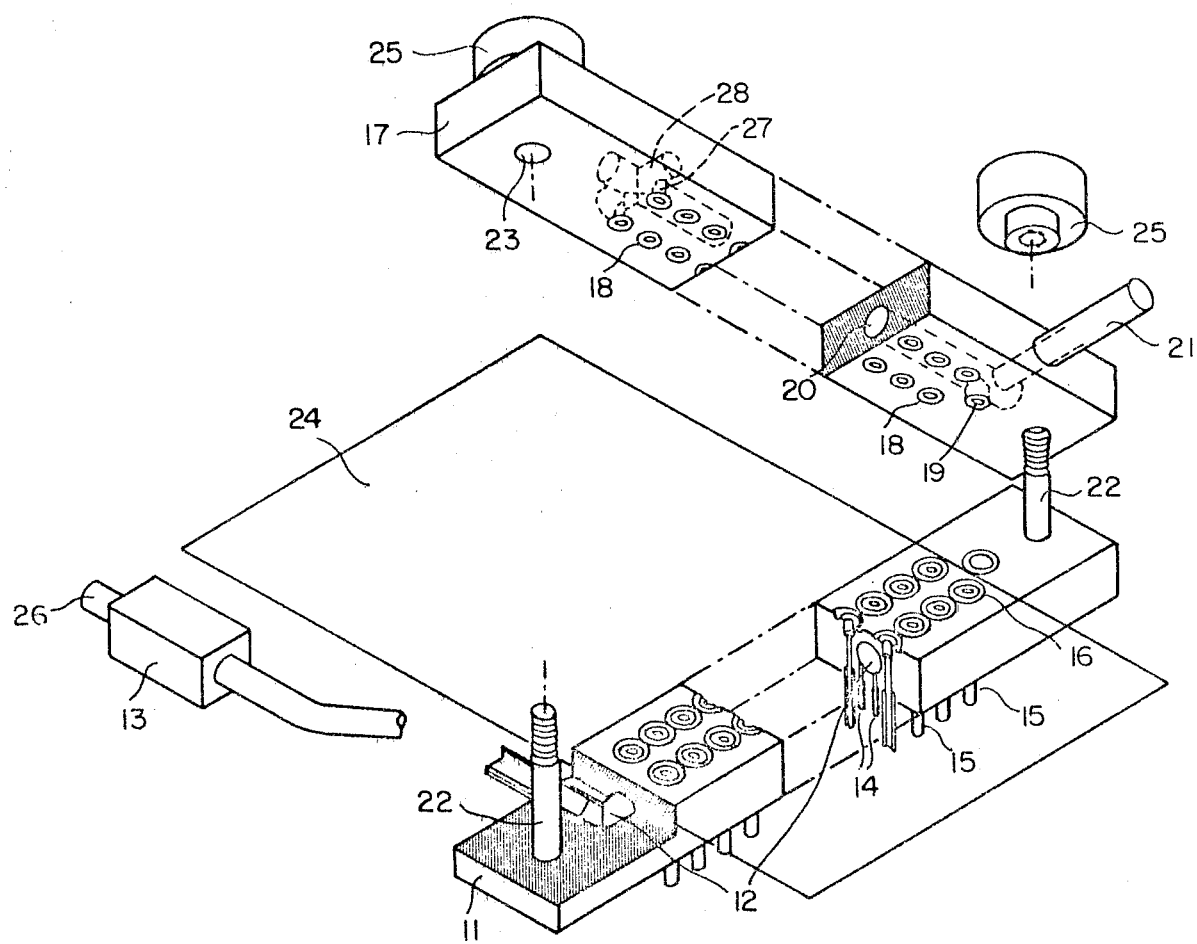
FIG. 1 of the enclosed drawing is an exploded perspective view, not according to scale, of a device according to the invention.

As illustrated in the enclosed drawing, the device according to the present invention comprises in combination a block 11, which forms the lower part of the device, which has a throughgoing conduit channel 12, connected with valve 13 which is connected directly with each of a source of washing fluid, not shown in the Figure. The said channel 12 is connected with 24 outlet tubelets 14 disposed within block 11. The spacing and configuration of the outlet tubes 14 is such that, when placed opposite a standard cultivation plate having two consecutive rows of twelve conventional size wells each, one of said tubelets 14 fits into each of the wells thereof. Once the valve 13 is activated, it can be seen that washing fluid will pass through channel 12 and tubelets 14 into each of the wells of the culture plate.

There are further provided 24 tubes 15, which protrude below the lower surface of block 11, and which terminate at its upper surface, where O-rings 16 are provided which serve to provide a tight fit towards the filter medium which is clamped between block 11 and the upper block 17. Upper block 17 has 24 tubular inlets 18, corresponding with the upper ends of the tubes 15 and an additional tubular inlet 19 (used for vacuum release). A conduit channel 20 is provided within the upper block 17. Channel 20 is connected to an outlet 21 which is connected to a vacuum source when in use. Each of the inlets 18 and 19 are connected to channel 20 by means of connecting channels 27 and 28. It can be seen, therefore, that when a vacuum is applied to outlet 21, suction is created at the bottom of each tube 15 through tubes 15 and, due to O-rings 16, channels 27, 28 and 20. Furthermore, if outlet 21 is connected to a vacuum source and valve 13 permits flow of washing fluid, washing fluid entering each of the wells via tubelets 14 will be aspirated into channel 20 by way of tubes 15.

There are provided two screws 22 extending upwards from block 11, and which fit through holes 23 in the upper block, and which make it possible to securely and tightly attach blocks 11 and 17 with each other. When in use a sheet of filter medium, such as a sheet of glass fiber filter paper 24 of suitable width, is clamped between blocks 11 and 17. The blocks are secured by means of bolts 25 and due to the provision of the O-rings 16 there is established an airtight fit between each of the tubes 15 in lower block 11 and the inlets 18 in upper block 17, with interposed filter paper 24.

When the device is to be used, the filter paper 24 is clamped between the two blocks 11 and 17, by tightening the bolts 25. The tubular outlet 21 is connected with a vacuum source and tube 26 of the valve 13 is connected with a bottle of washing solution. The unit is positioned over a microculture plate in such manner that each tube 14 and tube 15 occupy one well of the cultivation plate. It is clear that 24 wells can be harvested simultaneously. The cells are sucked through tubes 15 and are deposited on the filter paper 24, the content of each well being deposited on the area defined by one of the O-rings 16. The fluids are sucked through the upper block to a collection bottle. After this the valve 13 is opened, washing fluid is introduced into each of the wells of the culture plate by way of channel 12 and tubelets 14 and is sucked immediately through the filter by the vacuum source. After the completion of the desired washing, the blocks are unclamped, the vacuum is automatically released through inlet 19 and the filter paper is either removed or moved further on to provide the possibility to harvest a further couple of rows of wells. At the end, the filter paper is removed, the location of each crop of cells resulting from a certain well in the culture plate is clearly marked by the ring formed by the pressure of the O-rings, and after drying these are pushed out and analyzed by insertion into counting vials or by other means.

The advantage is in the simplicity of construction of the device and its easy operation. The necessity to provide a plurality of tubular connections is eliminated and there is provided but one vacuum source and one wash bottle, each of which is connected by a single tubular conduit to the block-shaped device.

It is clear that the device illustrated above can be varied at will so as to provide for the simultaneous harvesting of cells, particles, precipitates, etc. from any desired number of rows or parts of rows of microculture plates, test tubes, etc. The device is either made of metal or it can also be produced from plastic and metal.

Metallic devices (with conventional O-rings) are easily cleaned and sterilized, if required. Plastic devices tolerate washing solutions which are corrosive to metals.

The above description is by way of illustration only and various changes and modifications in the nature and arrangements of the components can be resorted to without departing from the scope and spirit of the invention.

We claim:

1. A device for harvesting cells from a plurality of cells of a standard cell culture plate, comprising:
   an upper block;
   a lower block, complementary with said upper block;
   attaching means for clamping said upper and lower blocks together with a tight fit;
   first conduit means, provided within said lower block, for carrying washing fluid from a source thereof;
   valve means, connected to said first conduit means, for controlling the flow of washing fluid therein;
   a plurality of tubelets connected at the upper ends thereof to said first conduit means, the lower ends thereof extending below the bottom of said lower block, said tubelets being so spaced such that each of them fits into a well of the culture plate when in use;
   a plurality of tubes, parallel with said tubelets, passing through said lower block, one end of each of said tubes extending below said lower block and the other end of each of said tubes terminating at a respective one of a plurality of outlets at the upper face of said lower block;
   second conduit means, provided within said upper block, for connecting each of the outlets of said tubes in said lower block with a source of vacuum, said second conduit means including a plurality of openings in the lower face of said upper block, said openings being so spaced as to be opposite one of said outlets in said lower block when in use; and
   a plurality of sealing means, one of said sealing means being disposed at each of said outlets, for creating a tight connection between said outlets in said lower block and said openings in said upper block when in use.

2. A device according to claim 1, further including a filter medium interposed between said lower and upper blocks, tightly secured therebetween by said attaching means.

3. A device according to claim 1, wherein said attaching means comprises screws and bolts.

4. A device in accordance with claim 1 wherein each said sealing means comprises an O-ring.

5. A method for the simultaneous harvesting of a plurality of individual cell cultures cultivated in the wells of a conventional microculture plate using the device in accordance with claim 1, comprising:
   inserting filter medium between said upper and lower blocks and clamping said blocks tightly together by means of said attaching means;
   positioning said device such that one of said tubelets and one of said tubes extend into each of the wells of the microculture plate;
   applying a vacuum to said second conduit means so as to aspirate the content of the wells to individual areas of said filter medium;
   introducing washing fluid into the wells by means of said first conduit means and said tubelets, which washing fluid is aspirated through said filter medium;
   disconnecting the vacuum; and
   removing the filter medium for subsequent treatment or analysis.

6. A method in accordance with claim 5 wherein each said sealing means comprises an O-ring, and each of the well contents on said filter medium is confined to an area surrounded by an O-ring.

* * * * *